US00PP15859P2

(12) United States Plant Patent
Olesen et al.

(10) Patent No.: US PP15,859 P2
(45) Date of Patent: Jul. 12, 2005

(54) FLORIBUNDA ROSE PLANT NAMED 'POULCS015'

(50) Latin Name: *Rosa hybrida*
Varietal Denomination: POULcs015

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 33 days.

(21) Appl. No.: 10/812,715

(22) Filed: Mar. 29, 2004

(51) Int. Cl.[7] ..... A01H 5/00
(52) U.S. Cl. ..... Plt./148
(58) Field of Search ..... Plt./148, 141, 107

*Primary Examiner*—Anne Marie Grunberg
*Assistant Examiner*—June Hwu

(57) ABSTRACT

A new garden rose plant of the floribunda class which has abundant, light pink flowers and attractive foliage. This new and distinct variety has shown to be uniform and stable in the resulting generations from asexual propagation.

2 Drawing Sheets

Botanical classification: *Rosa hybrida.*
Variety denomination: 'POULcs015'.

SUMMARY OF THE INVENTION

The present invention constitutes a new and distinct variety of garden rose plant which originated from a controlled crossing between the female parent plant named 'POULket' which is non-patented, and the male parent plant, an un-named seedling. The two parents were crossed during the summer of 1992 and the resulting seeds were planted in a controlled environment in Fredensborg, Denmark. The new variety is named 'POULcs015'.

The new variety may be distinguished from its female seed parent, 'POULket' by the following combination of characteristics:

1. While the seed parent 'POULket' has dark pink flowers, while 'POULcs015' has light pink flowers.
2. 'POULket' has a less compact growth habit than that of 'POULcs015'.

The new variety may be distinguished from its male pollen parent by the following combination of characteristics:

1. The pollen parent has a lower growing habit than 'POULcs015'.
2. The pollen parent does not grow well on its own roots, while 'POULcs015' flowers well and grows vigorously on its own roots.

The objective of the hybridization of this rose variety was to create a new and distinct variety for garden use with unique qualities, such as:

1. Uniform and abundant light pink flowers;
2. Vigorous, but compact growth when propagated both as a budded rose and on its own roots;
3. Disease resistance;
4. Continuous flowering.

This combination of qualities is not present in previously available commercial cultivars of this type, known to the inventors, and distinguish 'POULcs015' from all other varieties of which we are aware.

As part of their rose development program, L. Pernille Olesen and Mogens N. Olesen germinated the seeds from the aforementioned hybridization during winter of 1992 and conducted evaluations on the resulting seedlings in a controlled environment in Fredensborg, Denmark.

'POULcs015' was selected in the spring 1993 by the inventors as a single plant from the progeny of the aforementioned hybridization.

Asexual reproduction of 'POULcs015' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'POULcs015' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs015'. Specifically illustrated in Sheet 1:

FIG. 1.1; Open flower, stem showing cluster of open flowers, branching, and the attachment of leaves, buds, and peduncles;

FIG. 1.2; Flower bud closed, flower bud as sepals unfold, and partially open.

Specifically illustrated in Sheet 2:

FIG. 2.1; Sepals, receptacle, and peduncle;

FIG. 2.2; Flower petals, detached;

FIG. 2.3; Mature leaf, and juvenile leaf exhibiting anthocyanin;

FIG. 2.4; Juvenile stem and mature stem exhibiting thorns.

DETAILED DESCRIPTION OF THE VARIETY

The following is a description of 'POULcs015', as observed in its growth in a field nursery in Jackson County, Oreg. Observed plants were 3 years of age and were cultivated on *Rosa multiflora* understock. Color references are made using The Royal Horticultural Society (London, England) Colour Chart, 1995, except where common terms of color are used.

For a comparison, several physical characteristics of the rose variety 'POULasor', a rose variety from the same inventors described and illustrated in U.S. Plant patent application Ser. No. 10/339,871 dated Jan. 10, 2003, are compared to 'POULcs015' in Chart 1.

CHART 1

| | 'Poulcs015' | 'POULasor' |
|---|---|---|
| Petalage | 60 petals | 25 to 27 petals |
| Open flower: outer petal color, upper surface. | White Group 155C with light intonations of Red-Purple Group 73D at marginal zone | Red Group 55D |
| Bloom Diameter | 65 mm | 55 mm |

FLOWER AND FLOWER BUD

Blooming habit: Continuous.

Flower bud:

*Size.*—Upon opening, 25 mm in length from base of receptacle to end of bud. Flower bud diameter is 13 mm on average.

*Bud form.*—Pointed ovoid with very broad base.

*Bud color.*—As sepals unfold, petals are Orange Group 27B with intonations of Red Group 50B. At ¼ opening petals are Yellow-White Group 158C with Red Group 55B intonations.

*Sepals.*—

*Upper surface.*—Color: Green Group 138C with intonations of Greyed-Red Group 180A occurring at apecies. Lower surface: Color: Yellow-Green Group 144A. Anthocyanic pigments the color of Greyed-Red Group 181B observed. Texture: Smooth. Stipitate glands are scant. Sepal shape: Sepal apex is cirrhose. Base is flat at union with receptacle. Sepal margin: Margins have weak foliaceous appendages on three of the five sepals. Strongly pubescent. Size: 30 mm (l)×12 mm (w).

*Receptacle.*—Surface texture: Smooth and glabrous. Shape: Funnel shaped. Size: 8 mm (h)×7 mm (w). Color: Yellow-Green Group 144A. Anthocyanic pigments the color of Greyed-Red Group 181A observed.

*Pedicel.*—Surface: Smooth. Length: 40 to 45 mm. Diameter: 2.5 mm. Color: Yellow-Green Group 144B Anthocyanic pigments the color of Greyed-Red Group 181B observed. Strength: Strong.

*Peduncle.*—Surface: Smooth. Length: 120 to 150 mm. Diameter: 3 to 3.5 mm. Color: Yellow-Green Group 144B.

*Borne.*—In clusters of 12 flower buds per stem.

Flower bloom:

*Fragrance.*—Strong floral perfumed scent.

*Duration.*—The blooms have a duration on the plant of approximately 10 to 14 days. Petals fall cleanly away from plant.

*Size.*—Flower diameter is 65 mm when open. Flower depth is 50 mm on average.

*Form.*—General shape is a deep cup which retains a globular form.

Shape of flower when viewed from the side: Upon opening, upper part: Flat. Upon opening, lower part: Convex. Open flower, upper part: Flat. Open flower, lower part: Concave.

Petalage: 60 petals under normal conditions with an average of 25 petaloids.

Color:

Upon opening, petals:

*Outermost petals.*—Outer side: White Group 155C with intonations of Red-Purple Group 73B to 73C at the marginal zone. Inner side: White Group 155C with very light intonations of Red-Purple Group 73D at the marginal zone.

*Innermost petals.*—Outer side: Red-Purple Group 73C to 73B with intonations of White Group 155C at the basal zone. Inner side: Yellow-White Group 158C with intonations of Red Group 55C at the marginal zone.

Upon opening, basal petal spots: No distinctive coloration at the petal base observed.

After opening, petals:

*Outermost petals.*—Outer side: White Group 155C with Red-Purple Group 73C at the marginal zone. Inner side: White Group 155C with light intonations of Red-Purple Group 73D at the marginal zone.

*Innermost petals.*—Outer side: Red-Purple Group 73B to 73C with intonations of White Group 155C at the basal zone. Inner side: Yellow-White Group 158C with intonations of Red Group 55C at the marginal zone.

After opening, basal petal spots: No distinctive coloration at the petal base observed.

General tonality: On open flowers Red-Purple Group 73D to 73C with intonations of White Group 155C. No change in the general tonality at the end of the $10^{th}$ day.

Petals:

*Petal reflex.*—Somewhat reflexed.

*Margin.*—Entire and with point in center of margin. Weak undulations of margin observed.

*Shape.*—Apex is rounded, occasionally with a point or cleft. Base shape is acute.

*Size.*—50 mm (l)×38 mm (w).

*Texture.*—Smooth.

*Thickness.*—Average.

*Arrangement.*—Not Formal.

Petaloids:

*Quantity.*—20 to 30.

*Color.*—Upper surface: Red-Purple Group 73D. Lower surface: Red-Purple Group 73C.

*Size.*—23 mm (l)×10 mm (w).

*Shape.*—Base is acute. Apex is round.

Reproductive organs:

*Pistils.*—Length: 10 mm. Quantity: 59 (actual count).

*Pollen.*—None observed.

*Anthers.*—Size: 2 mm in length. Color: Yellow-Orange Group 14A. Quantity: 82 (actual count).

*Filaments.*—Color: Yellow Group 5B. Length: 7 mm.

*Stigmas.*—Superior relative to the length of filaments and the height of the anthers. Color: Yellow-White Group 158B.

*Styles.*—Color: Green-White Group 157C. Length: 7 to 10 mm. Other Intonations: Red-Purple Group 67A to Greyed-Purple Group 184D.

*Hips.*—None observed in the field nursery in Jackson County Oreg.

PLANT

Plant growth: Moderate, upright to bushy. When grown as a budded field grown plant on *Rosa multiflora* understock, the average height of the plant is 90 cm and the average width is 75 cm.

Stems:

*Color*.—Young wood: Yellow-Green Group 144B with anthocyanic intonations the color of Greyed-Orange Group 176C. Older wood: Yellow-Green Group 144B.

*Surface texture*.—Young wood: Smooth. Older wood: Smooth.

Thorns:

*Incidence*.—6 thorns per 10 cm of stem.

*Size*.—Average length: 9 mm.

*Color*.—Mature thorns are Yellow-Green Group 146C. Juvenile thorns are Greyed Red Group 181A.

*Shape*.—Deeply concave.

Plant foliage: Normal number of leaflets on normal leaves in middle of the stem: 5 leaflets.

*Compound leaf size*.—170 mm (l)×135 mm (w).

*Color*.—Mature foliage: Upper surface is: Yellow-Green Group 146A. Lower surface is: Yellow-Green Group 146C. Juvenile foliage: Upper surface is: Yellow-Green Group 146B. Lower surface is: Yellow-Green Group 146C. Anthocyanin: Location: New shoots, leaves, and juvenile flower buds. Color: Greyed-Red Group 178A.

Plant leaves and leaflets:

*Stipules*.—Size: 28 mm in length. Shape: Linear with outward extending apecies. Quantity: 2 per compound leaf. Color: Yellow-Green Group 144A.

*Petiole*.—Length: 40 mm. Diameter: 3 mm. Above: Color: Yellow-Green Group 144B. Underneath: Stipitate glands observed.

*Rachis*.—Length: 50 mm. Above: Color: Yellow-Green Group 144B. Underneath: Observations: Stipitate glands observed.

*Leaflet*.—Size: 65 to 75 mm (l)×45 to 57 mm (w). Edge: Serrated. Shape: Generally ovate. Base is rounded. Apex is mucronate. Thickness: Thick. Texture: Smooth. Arrangement: Odd pinnate. Venation: Reticulate. Glossiness: Moderately glossy.

Disease resistance: Above average resistance to mildew, rust, black spot, and *Botrytis* under normal growing conditions in Jackson County, Oreg.

Cold hardiness: The variety 'POULcs015' has been found to be cold tolerant to USDA Cold Hardiness Zone 6.

It is claimed:

1. A new and distinct variety of rose plant of the floribunda rose class named 'POULcs015', substantially as herein illustrated and described as a distinct and novel rose variety due to its abundant light pink flowers, disease resistance, and extended period of bloom.

* * * * *

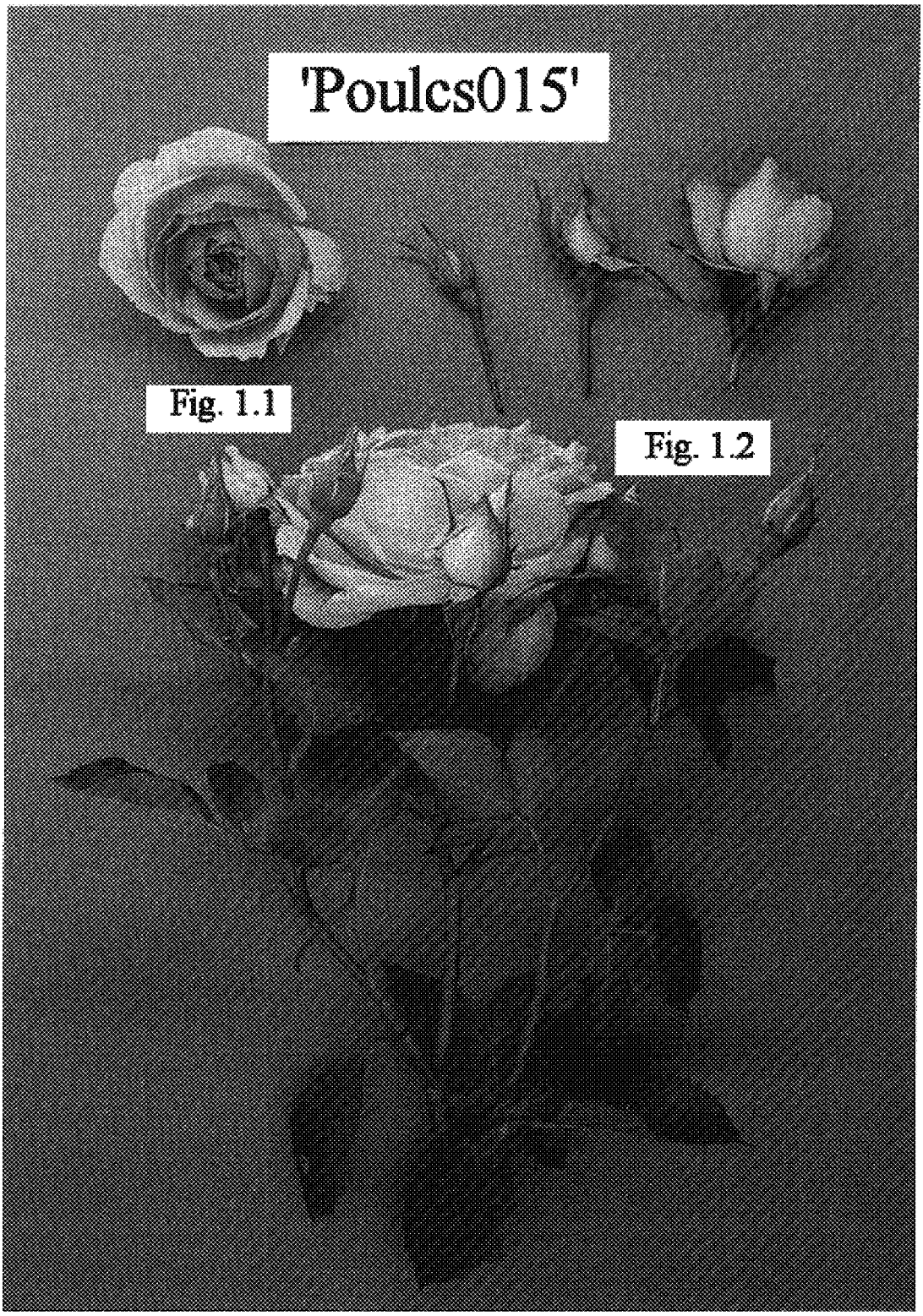
'Poulcs015'
Fig. 1.1
Fig. 1.2

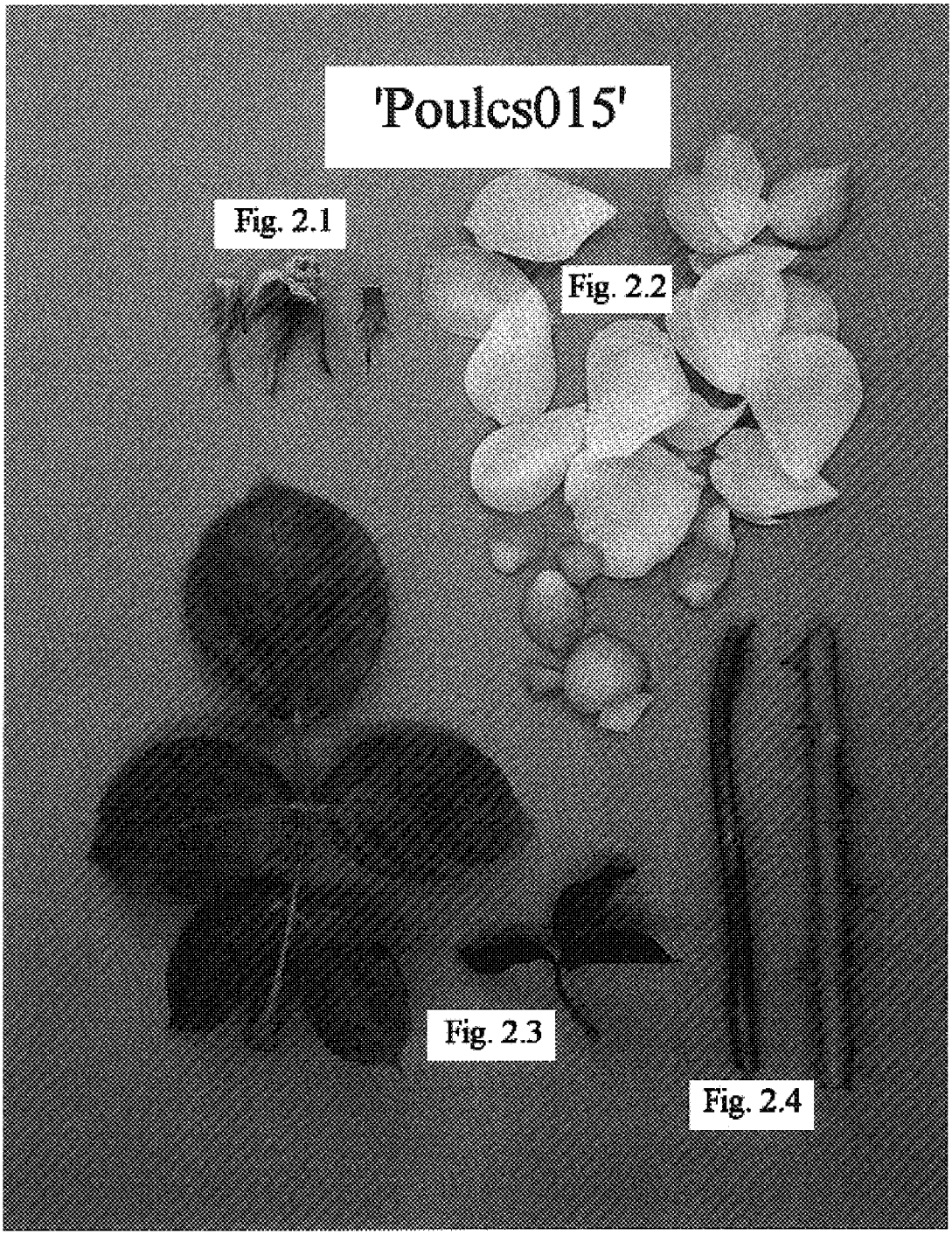
'Poulcs015'
Fig. 2.1
Fig. 2.2
Fig. 2.3
Fig. 2.4